United States Patent
Brown et al.

[19]

[11] Patent Number: 6,125,523
[45] Date of Patent: Oct. 3, 2000

[54] STENT CRIMPING TOOL AND METHOD OF USE

[75] Inventors: Daniel G. Brown, Temecula; Stephen A. Morales, Santa Clara, both of Calif.

[73] Assignee: Advanced Cardiovascular Systems, Inc., Santa Clara, Calif.

[21] Appl. No.: 09/196,534

[22] Filed: Nov. 20, 1998

[51] Int. Cl.⁷ .............................. B21D 39/04; B23P 11/00
[52] U.S. Cl. .................................. 29/516; 29/282; 72/90; 606/1
[58] Field of Search ................... 72/88, 90, 94; 29/516, 517, 270, 282, 283.5; 606/1

[56] References Cited

U.S. PATENT DOCUMENTS

| | | |
|---|---|---|
| 696,289 | 3/1902 | Williams . |
| 2,964,088 | 12/1960 | Erath .............................................. 72/90 |
| 4,455,854 | 6/1984 | Ermolovich .................................. 72/90 |
| 4,468,224 | 8/1984 | Enzmann et al. . |
| 4,576,142 | 3/1986 | Schiff . |
| 4,644,936 | 2/1987 | Schiff . |
| 4,681,092 | 7/1987 | Cho et al. . |
| 4,697,573 | 10/1987 | Schiff . |
| 4,901,707 | 2/1990 | Schiff . |
| 4,907,336 | 3/1990 | Gianturco ................................... 29/515 |
| 5,132,066 | 7/1992 | Charlesworth et al. . |
| 5,133,732 | 7/1992 | Wiktor ........................................ 606/1 |
| 5,183,085 | 2/1993 | Timmermans ............................ 140/89 |
| 5,189,786 | 3/1993 | Ishikawa et al. .......................... 29/283 |
| 5,437,083 | 8/1995 | Williams et al. ............................ 606/1 |
| 5,546,646 | 8/1996 | Williams et al. .......................... 29/516 |
| 5,626,604 | 5/1997 | Cottone, Jr. .............................. 606/108 |
| 5,630,830 | 5/1997 | Verbeek .................................... 606/108 |
| 5,653,691 | 8/1997 | Rupp et al. ............................... 606/194 |
| 5,672,169 | 9/1997 | Verbeek .................................... 606/1 |
| 5,725,519 | 3/1998 | Penner et al. . |
| 5,738,674 | 4/1998 | Williams et al. ............................ 606/1 |
| 5,746,764 | 5/1998 | Green et al. .............................. 606/108 |
| 5,759,474 | 6/1998 | Rupp et al. . |
| 5,783,227 | 7/1998 | Dunham . |
| 5,785,715 | 7/1998 | Schatz ........................................ 606/1 |
| 5,787,572 | 8/1998 | Toms ......................................... 29/282 |
| 5,810,873 | 9/1998 | Morales ..................................... 606/1 |
| 5,836,952 | 11/1998 | Davis et al. ............................ 606/108 |
| 5,920,975 | 7/1999 | Morales ................................... 29/282 |

FOREIGN PATENT DOCUMENTS

| | | |
|---|---|---|
| 630 623 A2 | 12/1994 | European Pat. Off. . |
| 826 346 A1 | 3/1998 | European Pat. Off. . |
| 0 873 731 A1 | 10/1998 | European Pat. Off. . |
| 0 938 877 A2 | 9/1999 | European Pat. Off. . |
| 464004 | 8/1928 | Germany .................................. 72/88 |
| 159065 | 1/1921 | United Kingdom . |
| WO 98/14120 | 4/1998 | WIPO . |
| WO 98/19633 | 5/1998 | WIPO . |

OTHER PUBLICATIONS

The eXTraordinary Stent, C.R. Bard Brochure (undated).

*Primary Examiner*—Daniel C. Crane
*Attorney, Agent, or Firm*—Fulwider Patton Lee & Utecht, LLP

[57] ABSTRACT

A hand held tool for crimping a stent onto a balloon of a catheter is disclosed. The stent crimping tool is operated in one hand by squeezing two plates together while simultaneously displacing the plates linearly to crimp and roll the stent held between the plates. Specifically, the crimping tool includes a base plate with two bosses through which respective pins pass linking the base plate to a compression plate. The compression plate has elongated diameter openings at opposite sides thereof to receive the pins. With the elongated diameter openings, the compression plate can pivot at the pins and translate linearly relative to those pins thus enabling the rolling action during the crimping process. A compression profile pad and a tapered profile pad are attached to the crimping areas of the plates to grip and together apply pressure to the uncrimped stent held therebetween. The pads may include specific contours in order to impart a desired profile to the crimped stent.

23 Claims, 4 Drawing Sheets

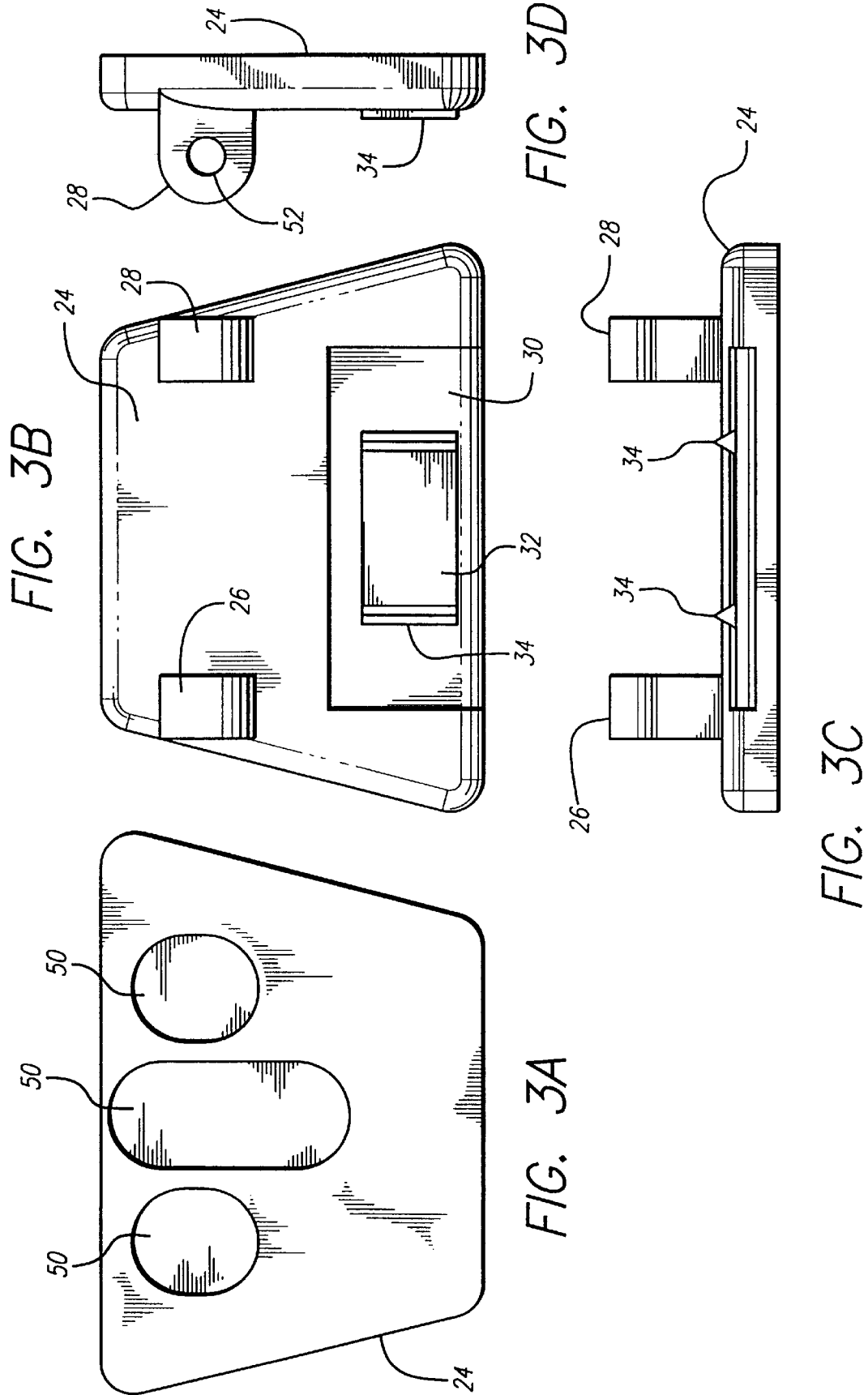

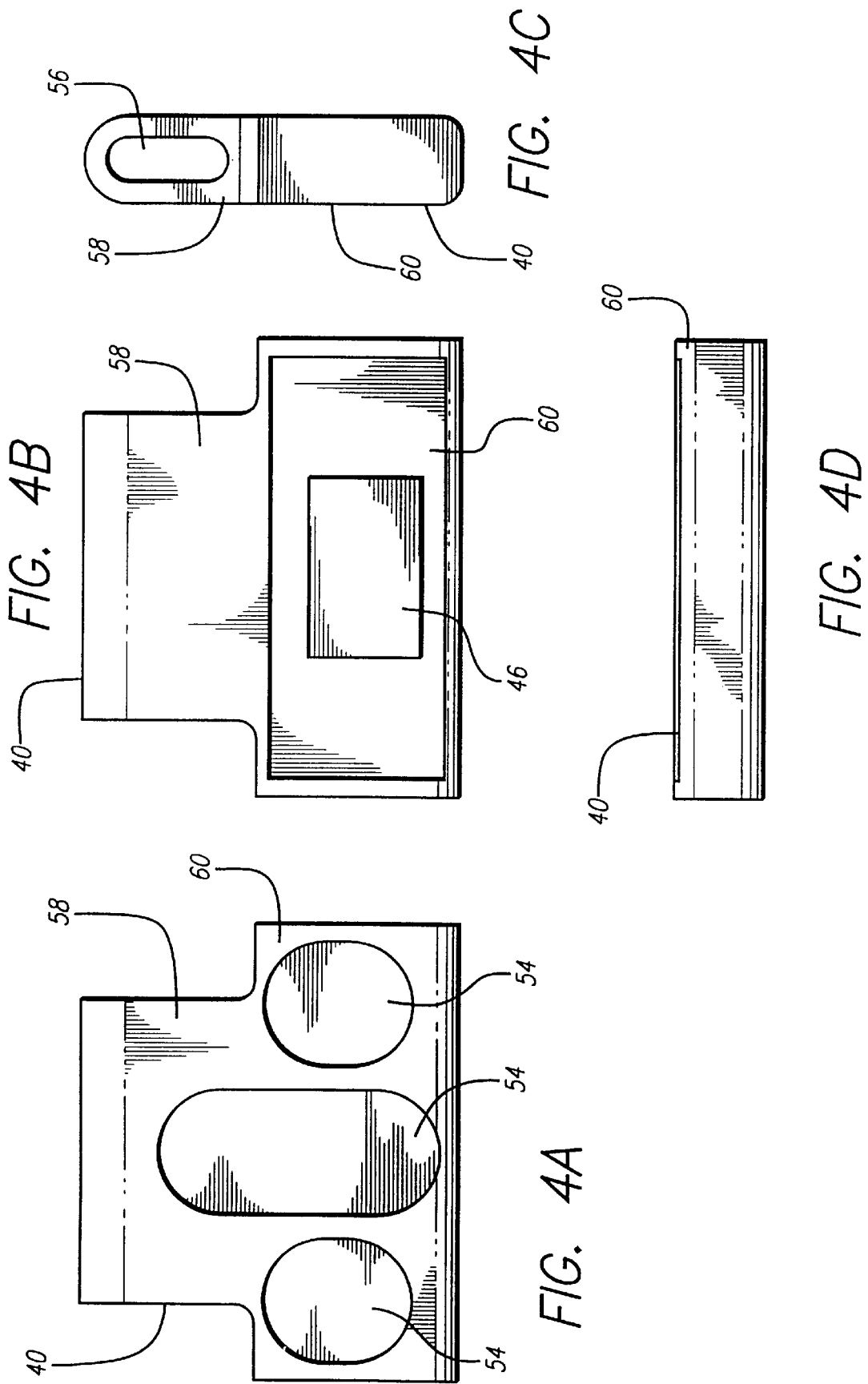

STENT CRIMPING TOOL AND METHOD OF USE

BACKGROUND OF THE INVENTION

The present invention relates to an apparatus for loading a tubular graft, such as a stent, onto the distal end of a catheter assembly of the kind used, for example, in percutaneous transluminal coronary angioplasty (PTCA) or percutaneous transluminal angioplasty (PTA) procedures.

In typical PTCA procedures, a guiding catheter is percutaneously introduced into the cardiovascular system of a patient through the brachial or femoral arteries and advanced through the vasculature until the distal end of the guiding catheter is in the ostium. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop over time, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the lesion. The stent is crimped tightly onto the balloon portion of the catheter and transported in its delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and probably through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, on rare occasions it is possible that the stent may slide off the catheter and into the patient's vasculature prematurely as a loose foreign body, possibly causing blood clots in the vasculature, including thrombosis. Therefore, it is important to ensure the proper crimping of a stent onto a catheter in a uniform and reliable manner.

This crimping is often done by hand, which can be unsatisfactory due to the uneven application of force resulting in non-uniform crimps. In addition, it is difficult to visually judge when a uniform and reliable crimp has been applied.

Some self-expanding stents are difficult to load by hand onto a delivery device such as a catheter. Furthermore, the more the stent is handled the higher the likelihood of human error, which would be antithetical to a properly crimped stent. Accordingly, there is a need in the art for a device for reliably crimping a stent onto a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, U.S. Pat. Nos. 5,437,083 and 5,546,646 to Williams et al.

Yet another stent crimping tool is known in the art as the BARD XT, which is actually a stent loader. It is constructed from a rigid, tubular body with a ball at one end connected to a plurality of long, thin strips passing through the tubular body. An uncrimped stent is placed over the plurality of long, thin strips, which hold the stent in an expanded state. The balloon portion of a catheter is inserted into the cylindrical space formed by the plurality of strips. When the user pulls the ball while holding the tubular body against the stent, the strips are slid from beneath the stent and the stent is transferred onto the balloon portion.

Still another conventional stent crimping tool is manufactured by JOHNSON & JOHNSON and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

While the prior art devices are suitable for crimping stents onto balloon catheters, they suffer from problems such as non-uniform crimping forces, resulting in non-uniform crimps. Consequently, they are unsuitable for use by physicians in a cath lab who desire to crimp the stent onto the balloon catheter.

SUMMARY OF THE INVENTION

Both PTCA and PTA procedures have become commonplace in treating stenoses or lesions in blood vessels and coronary arteries. In approximately 35% to 40% of the procedures, restenosis may develop requiring a further angioplasty, atherectomy or bypass procedure to return the patency of the vessel. Intravascular stents are now being deployed after PTCA and PTA procedures, and after atherectomies, in order to help prevent the development of restenosis. Importantly, such stents, mounted on the balloon portion of a catheter, must be tightly crimped to provide a low profile delivery diameter, and to ensure that the stent stays on the balloon until the balloon is expanded and the stent is implanted in the vessel. The present invention is directed to a crimping tool that can repeatedly provide a uniform and tight crimp to ensure the low profile diameter of the stent on the balloon portion of the catheter, and to ensure that the stent remains firmly attached until it is implanted in the vessel by expanding the balloon.

In a preferred embodiment, the present invention is directed to a tool for crimping a stent onto a balloon portion of a catheter, comprising a base plate having a press area and at least one boss; a compression plate having a press area, and an elongated opening; a pivot linking the boss and the elongated diameter opening so that the compression plate moves linearly and rotatably relative to a longitudinal axis of the pivot; and a tapered profile pad having ridges disposed on the press area of the base plate; whereby the stent is mounted on the balloon portion and aligned with the ridges of the tapered profile pad, and the compression plate is closed thereon to crimp the stent onto the balloon portion of the catheter.

In the preferred embodiment, the tool further comprises at least two bosses at opposite edges of the base plate, wherein each boss includes a circular hole; at least two cylindrical pins disposed in each boss and extending toward each other on a common axis; and at least two elongated diameter openings on opposite sides of the compression plate, receiving the two cylindrical pins so that the compression plate rotates and translates linearly relative to the common axis.

With such a construction, the present invention crimping tool is capable of imparting a crimping pressure radially by closing the compression plate onto the base plate thus pinching the stent-catheter assembly therebetween, and simultaneously rolling the stent-catheter assembly therebetween by translating or sliding the compression plate linearly relative to the base plate or a boss defining the common axis. The rolling action evenly distributes the crimping pressure to obtain a homogeneous and uniform crimp along the circumference of the stent.

In a preferred embodiment, the present invention crimping tool includes a compression profile pad having a raised surface disposed on the press area of the compression plate. It along with the tapered profile pad also having ridges disposed on the press area of the press plate impress the desired profile on the crimped stent. This is accomplished by first forming the desired profile into the special durometer polymer pads that engage the uncrimped stent-catheter assembly therebetween. When crimping pressure is applied and with the rolling of the stent by linear translation of the compression plate, the stent is slowly deformed according to the contours and profiles of the pads.

Beneficially, the contours of the pads grip the stent firmly and do not allow any damage to either the stent or the balloon catheter. Furthermore, the ridges on the tapered profile pad and the raised surface of the compression profile pad insure proper alignment of the stent on the balloon catheter and exact placement of the stent-catheter assembly inside the crimping tool.

During the crimping process, the compression plate is closed on the base plate under finger pressure thereby translating the finger squeeze pressure to radial crimping pressure. Also, the compression plate is translated linearly relative to the base plate to roll the stent-catheter assembly therebetween to evenly distribute the radial crimping pressure. These operations slowly reduce the diameter of the stent until it crimps tightly onto the balloon catheter.

As the stent nears its minimum diameter, the present invention contemplates applying a strong closing force while continuing to roll the stent between the plates. Typically, after three to five cycles of the foregoing operations, the crimping process is complete. The plates are opened and the stent-catheter assembly is removed and is ready for use.

During the process, some adjustment might be necessary to make sure the stent is crimped in the appropriate position on the balloon. By observing the stent-catheter assembly through the gap between the compression plate and the base plate, or by swinging the compression plate away from the base plate, the user or cardiologist can carefully monitor the progress of the crimping operation and assure proper alignment of the component parts.

Important to the movement of the compression plate is the presence of an elongated diameter opening. In the preferred embodiment, the elongated diameter opening includes a rectangular shape opening with opposed semi-circular edges into which a pin is inserted to interconnect the compression plate to the base plate. The elongated diameter opening, similar to a slot, allows the compression plate to translate linearly relative to the base plate as well as to pivot about an axis coinciding with the pin. Such a pivot may take many forms insofar as its construction enables both linear and rotational movement by the compression plate relative to the base plate.

Again, in the preferred embodiment, the exteriors of the compression plate and base plate may include finger grooves for easy gripping by the user or cardiologist. Using the finger grooves, the present invention crimping tool is preferably held in one hand between the thumb and index, middle, and third fingers. The uncrimped stent is mounted on the balloon portion of the catheter and then placed equally between the tapered ridges on the tapered profile pad. Finger pressure is then applied to the crimping tool as described above to crimp the stent.

The present invention tool can be used to crimp mounted or unmounted stents. The tool may further be used for production crimping of self-expanding stent designs. The present invention tool is intended for single-hand use, and it is of an ambidextrous design. Naturally, the overall size and shape of the tool may change to suit ergonomic, cosmetic, and manufacturing considerations.

The present invention crimping tool is thus highly useful to cardiologists, for example. Such physicians are constantly concerned with proper deployment of the stent within the patient that it is desirable to have a consistently and reliably crimped stent. The present invention tool is further a time saver in that the stent crimping procedure can be performed fairly efficiently and quickly. These and other advantages of the present invention will become apparent from the following detailed description thereof when taken in conjunction with the accompanying exemplary drawings.

BRIEF DESCRIPTION OF THE DRAWINGS

FIGS. 3A, 3B, 3C, and 3D are bottom and top plan views, and front and side elevational views of a preferred embodiment base plate in accordance with the present invention.

FIGS. 4A, 4B, 4C, and 4D are top and bottom plan views, and side and front elevational views of a preferred embodiment compression plate constructed in accordance with the present invention.

DETAILED DESCRIPTION OF THE PREFERRED EMBODIMENTS

Figure 1:
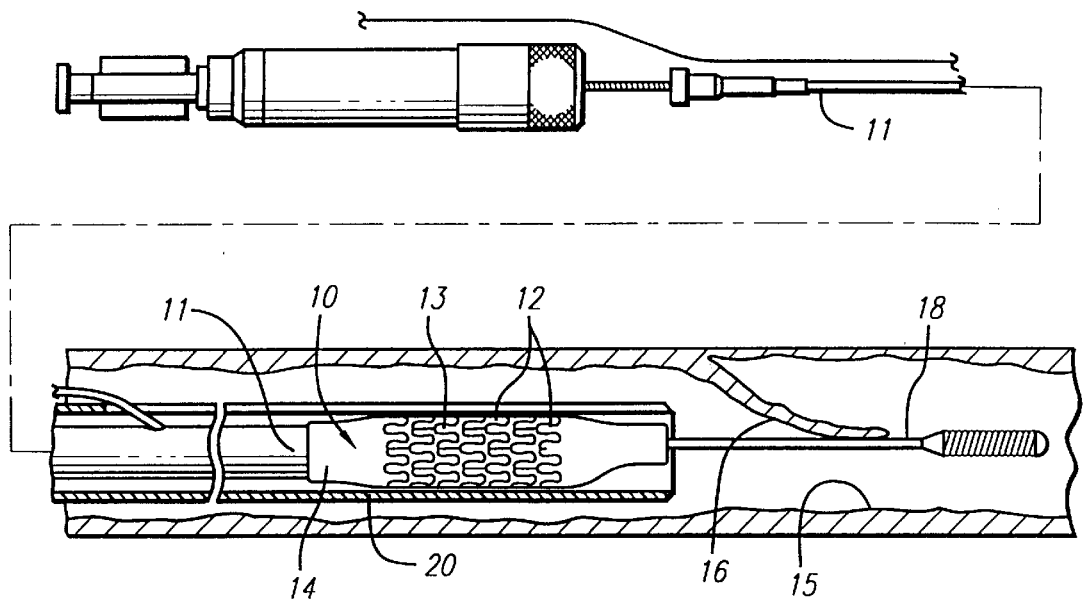
FIG. 1 is a side elevational view, partially in section, depicting a stent that has been crimped onto a delivery catheter and disposed within a damaged vessel.

FIG. 1 illustrates intravascular stent 10 which is mounted onto delivery catheter 11. Stent 10 generally comprises a plurality of radially expandable cylindrical elements 12 disposed generally coaxially and interconnected by members 13 disposed between adjacent cylindrical elements 12. Delivery catheter 11 has an expandable portion or balloon 14 for expanding stent 10 within coronary artery 15 or other vessel such as saphenous veins, carotid arteries, arteries, and veins. Artery 15, as shown in FIG. 1, has dissected lining 16 which has occluded a portion of the arterial passageway.

Delivery catheter 11 onto which stent 10 is mounted is known in the art and is essentially the same as a conventional balloon dilatation catheter for angioplasty procedures. Balloon 14 may be formed of suitable materials such as polyethylene teraphalate, polyethylene, nylon, polyvinyl chloride, and other like polymers. In order for stent 10 to remain in place on balloon 14 during delivery to the site of the damage within artery 15, stent 10 is compressed onto balloon 14. This compressing step is known as crimping.

An optional retractable protective delivery sleeve 20 may be provided to further ensure that stent 10 stays in place on balloon 14 of delivery catheter 11 and to prevent abrasion of the body lumen by the open surface of stent 10 during delivery to the desired arterial location. Other means for securing stent 10 onto balloon 14 may also be used, such as providing collars or ridges on the ends of the working portion, i.e., the cylindrical portion of balloon 14. In order to implant stent 10, it is first mounted onto inflation balloon 14 on the distal extremity of delivery catheter 11. Stent 10 is crimped down onto balloon 14 to ensure a low profile. The present invention addresses this crimping procedure.

The stent-catheter assembly can be introduced into the patient's vasculature through processes known in the art. Briefly, guide wire 18 is disposed across the arterial section where an angioplasty or atherectomy has been performed requiring a follow-up stenting procedure. In some cases, the arterial wall lining may be detached so that guide wire 18 is advanced past detached or dissected lining 16 and the stent-catheter assembly is advanced over guide wire 18 within artery 15 until stent is directly under detached lining 16. Prior to inflation of balloon 14, delivery sleeve 20 is retracted to expose stent 10. Depending on the balloon and stent assembly, a delivery sleeve may be unnecessary. Balloon 14 of delivery catheter 11 is then inflated using an inflation fluid. Expansion of balloon 14 in turn expands stent 10 against artery 15. Next, balloon 14 is deflated and catheter 11 is withdrawn leaving stent 10 to support the damaged arterial section. As mentioned above, in order to ensure proper seating of stent 10 on balloon 14, and to ensure proper deployment of stent 10 at the site of the damage within artery 15, the stent crimping procedure is important.

Figure 2:
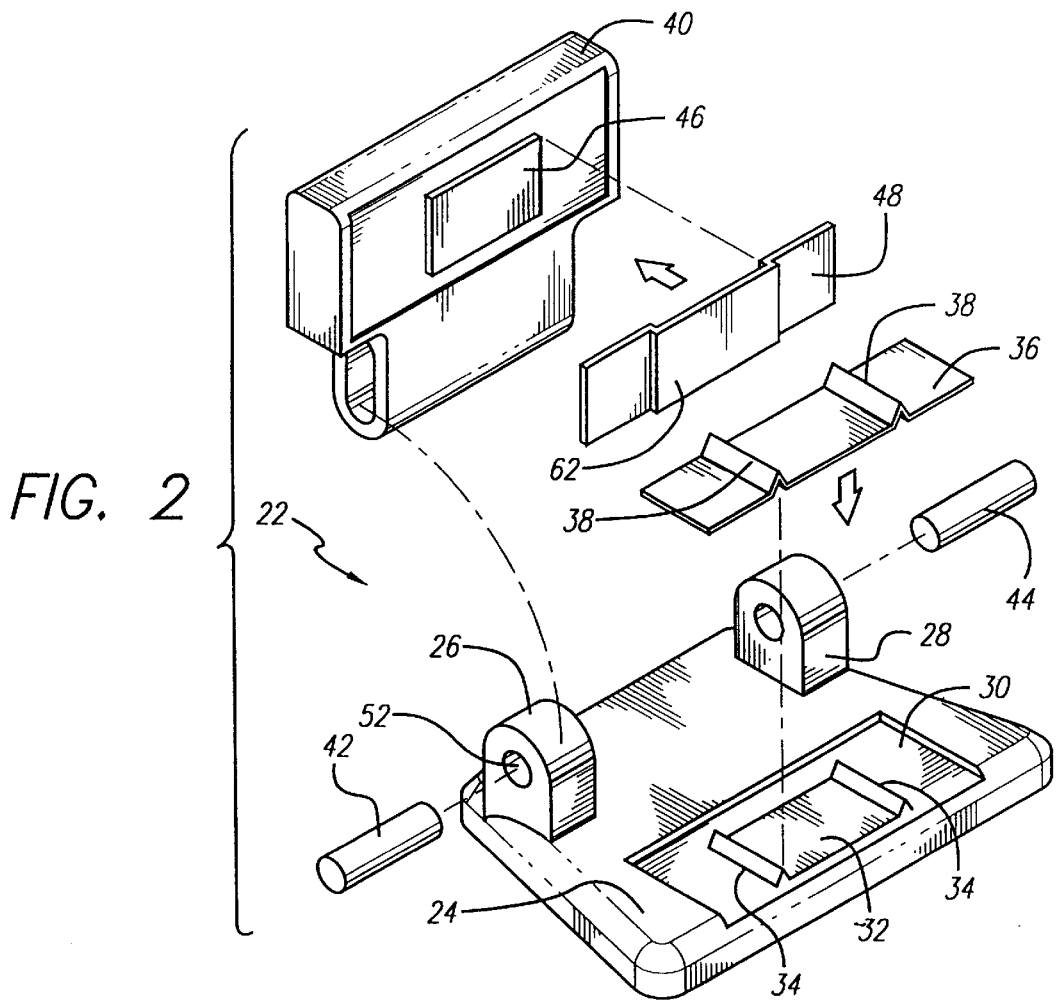
FIG. 2 is an exploded, perspective view of a preferred embodiment of the present invention stent crimping tool.

FIG. 2 is an exploded, perspective view of a preferred embodiment stent crimping tool 22. Stent crimping tool 22 includes a tapered or trapezoidal shape base plate 24 which optionally includes two bosses 26, 28 spaced apart at an edge, preferably back edge, of base plate 24. Base plate 24 further includes optional recessed work area 30 having disposed at a central location thereon raised press area 32. Raised press area 32, which functions as a platform, has ridges 34 that are spaced apart to approximate the length of a crimped stent. Disposed on top of press area 32 is tapered profile pad 36, also having ridges 38 overlying ridges 34 of press area 32. Because tapered profile pad 36 is made from a material that is somewhat resilient, its ridges 38 are supported from underneath by the more rigid ridges 34 of press area 32.

FIG. 2 also shows a perspective view of compression profile plate 40 which is pivotably attached to two lugs or bosses 26,28 by use of cylindrical pins 42, 44. Compression profile plate 40 includes an underside with press area 46 to which is attached compression profile pad 48. Compression profile pad 48 has resilience and functions as the counterpart to tapered profile pad 36, the two pads pinching the stent-catheter assembly therebetween during the crimping operation.

As indicated by the arrows, pins 42, 44 are inserted into the respective apertures or openings 52 in bosses 26, 28 to pivotably link base plate 24 to compression profile plate 40. The arrows in FIG. 2 also indicate that compression profile pad 48 is attached to and overlies press area 46 while tapered profile pad 36 is attached to and overlies raised press area 32.

To illustrate a crimping tool component in greater detail, FIGS. 3A–3D provide bottom and top plan views and front and side elevational views, respectively, of a preferred embodiment of base plate 24 shown in FIG. 2. Most prominent of the features of base plate 24 are vertically extending bosses 26, 28, as best seen in FIGS. 3C and 3D, and finger grooves 50 along the underside of base plate 24 as shown in FIG. 3A. Raised press area 32 has ridges 34 that are best seen in the front and side elevational views of FIGS. 3C and 3D, respectively. In the side elevational view of FIG. 3D, boss 28 includes opening 52 to receive cylindrical pin 44. Bosses 26,28 thus function as lugs to connect base plate 24 to compression profile plate 40. In addition, there are preferably two bosses 26, 28 in order to minimize torque and resultant shifting of compression plate 40 relative to base plate 24, which would cause imprecision in the crimping operation.

To show another crimping tool component in detail, FIGS. 4A–4D provide top and bottom plan views and side and front elevational views, respectively, of compression profile plate 40. In the top plan view of FIG. 4A, the top surface of compression profile plate 40 is exposed showing optional finger grooves 54. The underside of compression profile plate 40 includes press area 46 used for application of pressure to the uncrimped stent.

As best seen in the side elevational view of FIG. 4C, compression profile plate 40 features an elongated diameter opening 56 intended to receive cylindrical pins 40, 44 therethrough. Thus, back section 58 is narrow and fits between bosses 26, 28 of base plate 24 to allow compression profile plate 40 to rotate and slide linearly relative to an imaginary centerline or axis of cylindrical pins 42, 44. Front section 60 is designed to be wide to accommodate a user's hand, and the spaced apart finger grooves 54 improve grip and pressure control by the user's fingers or thumb.

As best seen in the exploded perspective view of FIG. 2, tapered profile pad 36 engages uncrimped stent 10 and its ridges 38 help align stent 10 within crimping tool 22 during the crimping process. Similarly, compression profile pad 48 includes raised surface 62 that engages uncrimped stent 10 during the crimping process. Specific contours or profiles may be formed into raised surface 62 or the area between ridges 38 on tapered profile pad 36 in order to impart that profile to uncrimped stent 10. Moreover, compression profile pad 48 and tapered profile pad 36 may be replaced with materials of varying durometers and proportions to accommodate stents of varying dimensions and hoop strengths. Thus, the present invention has replaceable pads 36, 38 that can be used to accommodate a large variety of stent designs.

Figure 5A:
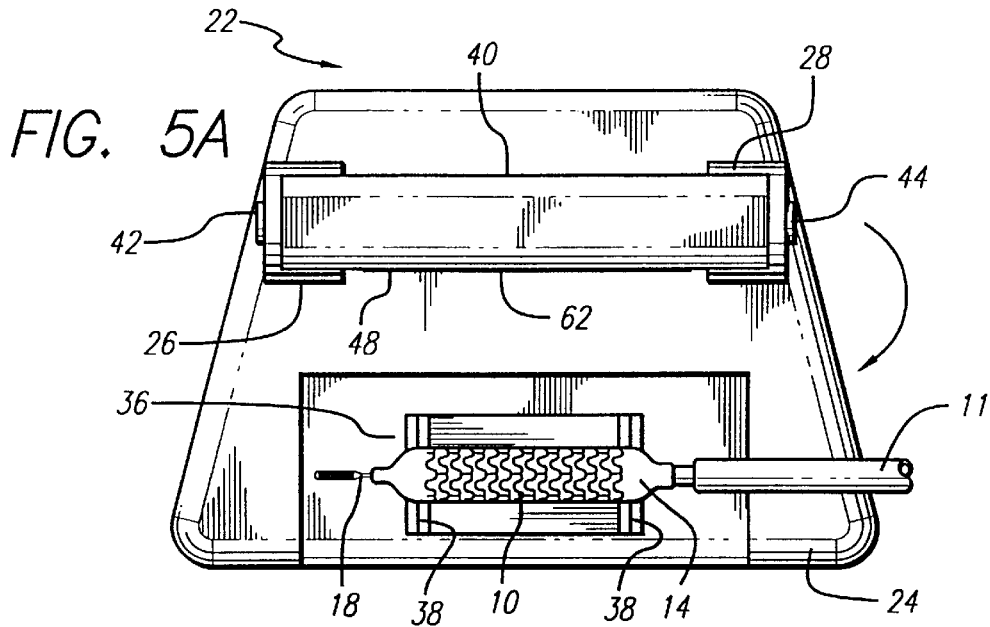
FIGS. 5A, 5B, and 5C are plan views of the present invention tool during the crimping process including closing the compression plate onto the base plate with the stent-catheter assembly therebetween as seen in FIG. 5A, and linearly translating the compression plate relative to the base plate to roll the stent-catheter assembly as seen in FIGS. 5B and 5C.
Figure 5B:
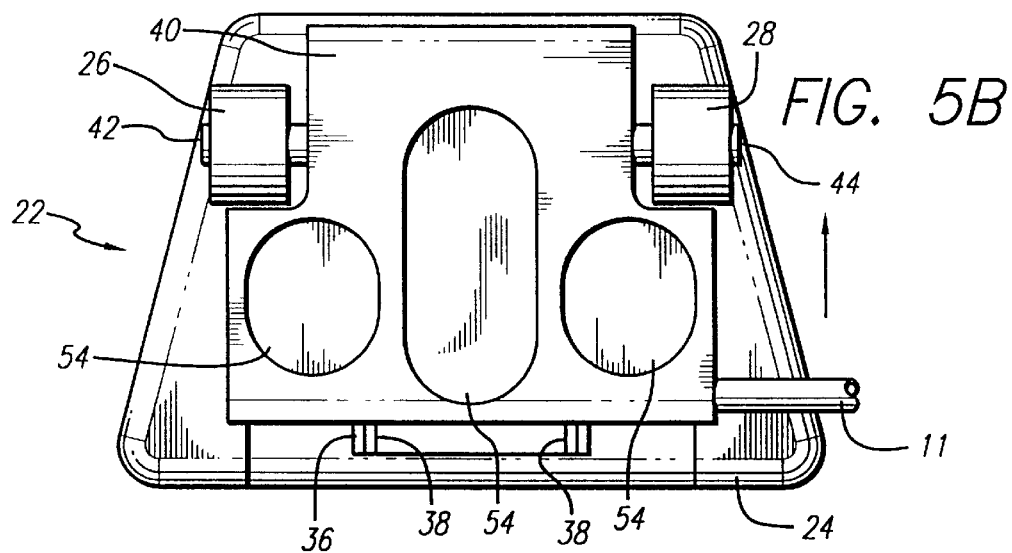
Figure 5C:
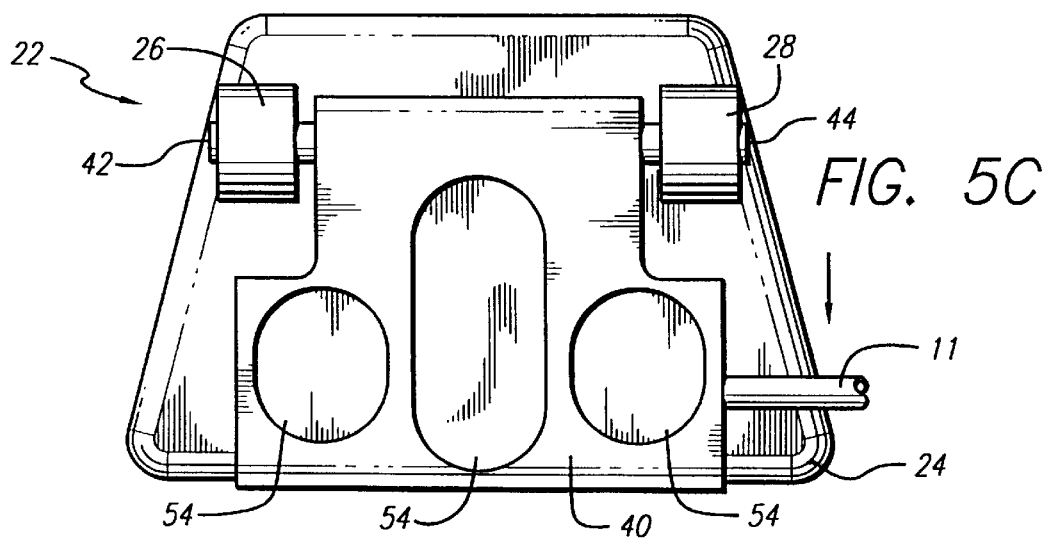

FIGS. 5A–5C provide plan views of the present invention stent crimping tool 22 during a stent crimping operation. FIG. 5A illustrates when compression profile plate 40 is closed onto the stent-catheter assembly as indicated by the curved arrow. FIGS. 5B and 5C illustrate the rolling of the stent-catheter assembly by linearly translating compression profile plate 40 relative to base plate 24, as suggested by the arrows.

In particular, FIG. 5A shows in plan view the open position of compression profile plate 40. As depicted here, stent 10 is laid across tapered profile pad 36 so that the distal and proximal ends of stent 10 are aligned with ridges 38. Catheter 11 then preferably extends out one side of crimping tool 22. Pins 42 and 44 pivotably link compression profile plate 40 to base plate 24 via bosses 26, 28.

As compression profile plate 40 is slowly closed onto stent 10, raised surface 62 of compression profile pad 48 engages the outer circumference of 10 uncrimped stent 10. This action is indicated by the bowed arrow in FIG. 5A.

In the plan view of FIG. 5B, compression profile plate 40 has assumed the closed position and is applying radial pressure to uncrimped stent 10 that is pinched between it and base plate 24. In the condition shown in FIG. 5B, compression profile plate 40 is in its farthest back position, while in the plan view of FIG. 5C, compression profile plate 40 is in the farthest forward position as indicated by the up and own arrows, respectively. This linear translation is possible due to the presence of elongated diameter openings 56 on either side of back section 58, which openings 56 permit linear translation as well as pivotal motion of compression plate 40 about the imaginary centerline of cylindrical pins 42, 44. Accordingly, FIGS. 5A–5C provide a simplified view of the present invention crimping process of closing compression profile plate 40 onto uncrimped stent 10 and applying radial pressure thereto, and the rolling operation achieved by linearly translating compression profile plate 40 relative to base plate 24.

Crimping tool 22 is gripped preferably in one hand and is designed for ambidextrous use. Finger grooves 50, 54 on the outer surfaces of compression profile plate 40 and base plate 24 permit the user or cardiologist to exert precise radial pressure and control the rolling action. This in turn results in homogeneous, precise, and repeatable crimps. Moreover, compression profile pad 48 and tapered profile pad 36 are carefully contoured to complement each other to prevent over-crimping of stent 10 onto balloon 15. Indeed, ridges 34 of tapered profile 36 may optionally be designed to engage raised surface 62 thereby setting a gap distance between compression profile plate 40 in its closed position against base plate 24. This gap therefore defines the finished or crimped outside diameter of stent 10.

In various alternative embodiments (not shown) the components enabling compression profile plate 40 to pivot and translate linearly relative to base plate 24 can be modified. For example, it may be possible to use a single boss on the base plate with a single pin engaging an elongated diameter opening in the side of the compression profile plate. In another alternative embodiment, cylindrical pins 42, 44 may be omitted in favor of ears or tabs extending out the sides of the compression profile plate at the back section thereof and engaging the openings in the bosses of the base plate.

In still another alternative embodiment, cylindrical pins 42, 44 are again omitted. To achieve the pivoting function, the interior, opposed faces of the bosses may be modified with bumps, cone shape projections, and the like, that extend into and engage elongated diameter openings 56 on either side of back section 58 thereby pivotably and slideably linking the compression profile plate to the base plate.

Of course, pins 42, 44 may be replaced with a single rod that extends through openings 52 of bosses 26, 28 and also passes through elongated diameter opening 56 which is now a through-hole to link the compression profile plate to the base plate. In yet another alternative embodiment, the bosses may have open tops that allow pins extending from the back section of the compression profile plate to snap in vertically. The present invention further contemplates use of more than one boss to improve stability and to resist torque on compression profile plate 40.

To use the present invention, the cardiologist or user holds crimping tool 22 in one hand between the thumb and index, middle, and third fingers. Stent 10 is mounted on balloon 14 and the stent-catheter assembly is placed equidistant between ridges 38 of tapered profile pad 36. Compression profile plate 40 is then gently closed onto the stent-catheter assembly until contact is made. Crimping starts as radial pressure is applied to stent 10 by compression profile plate 40 and by linear movement back and forth over stent 10 by compression profile plate 40. The closing pressure .is increased slowly while the back and forth motion of plates 24, 40 rolls the stent-catheter assembly circumferentially to evenly distribute crimping pressure. Consequently, the diameter of stent 10 slowly decreases until it crimps tightly onto balloon 14.

As stent 10 nears its minimum diameter, a strong closing force is optionally applied while continuing to move plates 24,40 to and fro. After preferably three to five cycles, the present invention crimping process is complete. Plates 24,40 are opened and the stent-catheter assembly is removed and is ready for use. Preferably, the crimping pressure initially applied by plates 24, 40 is very low and steadily increases. The user or cardiologist should also observe the rolling action to minimize the chance that the stent-catheter assembly might roll out of alignment with the travel of compression plate 40. This might cause an unintended distortion in the crimp.

It is clear that the overall size and shape of the present invention tool 22 may be changed to suit ergonomic, cosmetic, and manufacturing considerations. The present invention may be constructed from materials that are biocompatible and suitable for E-beam sterilization. To that end, the various components of the present invention crimping tool 22 may be made from a material such as Delrin. Tapered profile pad 36 and compression profile pad 48 may be fabricated from various durometer polymers or elastomers.

As will be appreciated by those skilled in the art, the present invention crimping tool 22 is designed for both single use applications in a cath lab by a physician, and for multiple use applications in a sterile environment in a high volume manufacturing facility. In such a manufacturing facility where sterile conditions exist, stent crimping tool 22 can be used to repeatedly crimp stents onto balloons until the mechanism wears out. Thus, repeated uses of the present invention are contemplated for controlled, sterile environments, although single use applications are required when used by cath lab personnel.

Furthermore, the present invention crimping tool can be used with any stent that is released without a delivery system. The crimping tool may also be sold alone because its design is robust enough to undergo many uses.

Other modifications can be made to the present invention without departing from the scope thereof. The specific dimensions, shapes, cycles, and materials of construction are provided as examples and substitutes are readily contemplated which do not depart from the invention.

What is claimed is:

1. A tool for crimping a stent on to a balloon portion of a catheter, comprising:
   a base plate having a press area and at least one boss;
   a compression plate having a press area, and an elongated diameter opening;
   a pivot linking the boss and the elongated diameter opening so that the compression plate moves linearly and rotatably relative to a longitudinal axis of the pivot; and
   a tapered profile pad having ridges disposed on the press area of the base plate;
   whereby the stent is mounted on the balloon portion and aligned with the ridges of the tapered profile pad, and the compression plate is closed thereon to crimp the stent on to the balloon portion.

2. The crimping tool according to claim 1, wherein the elongated diameter opening includes a rectangular shape opening with opposed semicircular edges.

3. The crimping tool according to claim 1, wherein the tool further comprises:
   at least two bosses at opposite edges of the base plate, wherein each boss includes a circular aperture;
   at least two cylindrical pins disposed in each boss and extending toward each other on a common axis; and
   at least two elongated diameter openings on opposite sides of the compression plate, receiving the two cylindrical pins so that the compression plate rotates and translates linearly relative to the common axis.

4. The crimping tool according to claim 1, wherein the tool further comprises a compression profile pad having a raised surface disposed on the press area of the compression plate.

5. The crimping tool according to claim 1, wherein the base plate has a tapered shape.

6. The crimping tool according to claim 1, wherein the base plate includes an exterior surface with a finger groove.

7. The crimping tool according to claim 1, wherein the compression plate includes an exterior surface with a finger groove.

8. The crimping tool according to claim 1, wherein the pivot includes a pin.

9. The crimping tool according to claim 1, wherein the press area of the bottom plate includes ridges separated by a length of the stent.

10. A tool for crimping a stent on to a balloon portion of a catheter, comprising:
    a base plate having a press area and at least two bosses with one boss on each side of the base plate, and each boss including a hole;
    a compression plate having a press area, and an elongated diameter opening on each side;
    a compression profile pad disposed to an underside of the compression plate, wherein the compression profile pad is contoured with a profile of a crimped stent;
    at least one pin engaging the bosses and the elongated diameters such that the elongated diameters enable the compression plate to move linearly and rotationally about a longitudinal axis of the pin; and
    a tapered profile pad having ridges disposed on the press area of the base plate;
    whereby the stent is mounted on the balloon portion and aligned with the ridges of the tapered profile pad, and the compression plate is closed thereon to crimp the stent on to the balloon portion.

11. The crimping tool according to claim 10, wherein the base plate includes a tapered shape proportionate to a length of the stent.

12. The crimping tool according to claim 10, wherein the ridges of the tapered profile pad define a finished length of a crimped stent.

13. The crimping tool according to claim 10, wherein the compression plate includes an exterior surface and the base plate includes an exterior surface, wherein each exterior surface includes a finger groove.

14. The crimping tool according to claim 10, wherein the press area of the base plate includes ridges aligned with the ridges of the tapered profile pad.

15. The crimping tool according to claim 10, wherein the compression profile pad and the tapered profile pad define a profile to be imparted to the stent.

16. A method for crimping a stent on to a balloon portion of a catheter, comprising the steps of:
    providing a base plate having a press area and at least one boss;
    providing a compression plate having a compression profile pad with a press area, and an elongated diameter opening;
    pivotably linking the boss to the elongated diameter opening so that the compression plate moves linearly and rotatably relative to the base plate; and
    providing a tapered profile pad having ridges disposed on the press area of the base plate;
    mounting the stent on the balloon portion;
    aligning the stent mounted on the balloon with the ridges of the tapered profile pad; and
    closing the compression plate to crimp the stent to the balloon between the compression profile pad and the tapered profile pad.

17. The method for crimping a stent according to claim 16, wherein the step of providing a base plate further comprises providing a boss with a bump to pivotably engage the elongated diameter opening.

18. The method for crimping a stent according to claim 16, wherein the method further comprises providing a pin to pivotably link the boss of the base plate to the elongated diameter opening of the compression plate.

19. The method for crimping a stent according to claim 16, wherein the method further comprises rolling the stent by translating the compression plate linearly relative to the longitudinal axis of the pin.

20. The method for crimping a stent according to claim 19, wherein the steps of rolling the stent and closing the compression plate are performed simultaneously.

21. The method for crimping a stent according to claim 19, wherein the steps of closing the compression plate and translating the compression plate are repeated.

22. The method for crimping a stent according to claim 16, wherein the step of closing the compression plate includes applying an increasing force to the compression plate.

23. The method for crimping a stent according to claim 16, wherein the method further comprises the step of gripping the base plate and the compression plate in one hand.

* * * * *